United States Patent
Hill et al.

[19]

[11] Patent Number: 5,971,981
[45] Date of Patent: Oct. 26, 1999

[54] HIGH FREQUENCY SURGICAL APPARATUS AND METHOD OF ITS OPERATION

[75] Inventors: Wolfram Hill, Freiburg; Konstantin Dornhof, Immendingen-Zimmern, both of Germany

[73] Assignee: Gebrueder Berchtold GmbH, Tuttlingen, Germany

[21] Appl. No.: 08/953,169

[22] Filed: Oct. 17, 1997

[51] Int. Cl.⁶ ................................................. A61B 17/38
[52] U.S. Cl. .............................................................. 606/35
[58] Field of Search .................................. 606/32, 33, 34, 606/35, 41, 42; 128/908

[56] References Cited

U.S. PATENT DOCUMENTS

| | | | |
|---|---|---|---|
| 4,741,334 | 5/1988 | Irnich | 606/35 |
| 4,754,757 | 7/1988 | Feucht | 606/35 |
| 4,788,977 | 12/1988 | Farin et al. | 606/35 |
| 4,848,335 | 7/1989 | Manes . | |
| 5,087,257 | 2/1992 | Farin et al. | 606/35 |
| 5,312,401 | 5/1994 | Newton et al. | 606/35 |
| 5,480,399 | 1/1996 | Hebborn . | |

*Primary Examiner*—Linda C. M. Dvorak
*Assistant Examiner*—Rosiland Kearney
*Attorney, Agent, or Firm*—Townsend and Townsend and Crew LLP

[57] ABSTRACT

The invention provides a radiofrequency surgical apparatus comprising a high frequency generator having at least one active electrode output and at least one neutral electrode output to which a part neutral electrode of a neutral electrode pair can be connected, with individual electrodes of the neutral electrode pair being connected to an auxiliary voltage with a significantly lower frequency than the high frequency. A monitoring circuit produces from the auxiliary voltage and the auxiliary current flowing between the part neutral electrodes an impedance signal representative for the impedance between the two part neutral electrodes and transmits a high frequency generator blocking signal and/or an alarm signal on exceeding a first fixed upper alarm limit and/or a lower second upper alarm limit for the impedance signal which can be matched to the actual value of the impedance signal. The adaptation of the second alarm limit is effected by pressing a SET key.

22 Claims, 2 Drawing Sheets

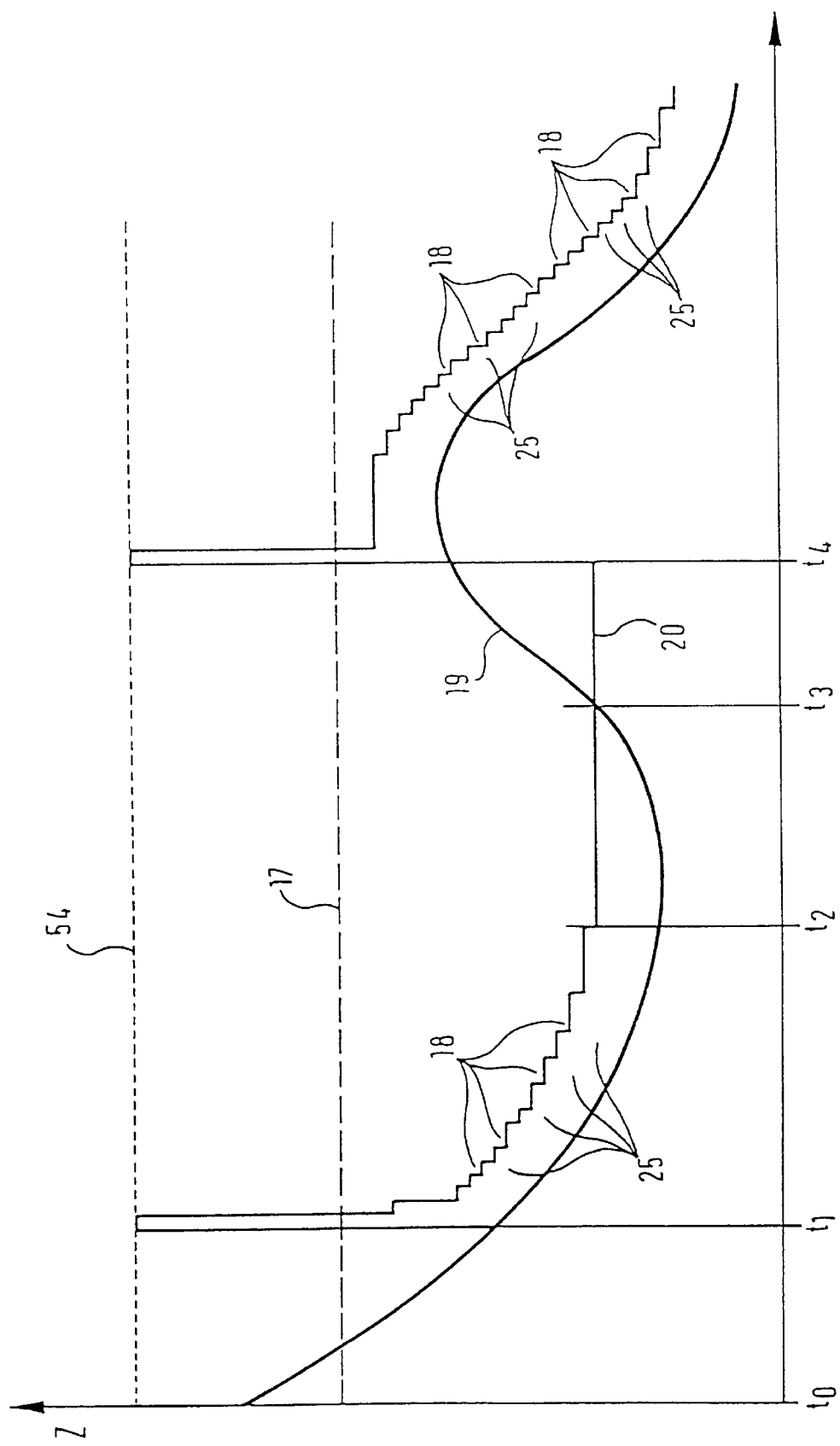

HIGH FREQUENCY SURGICAL APPARATUS AND METHOD OF ITS OPERATION

FIELD OF THE INVENTION

The invention relates to a method of operating a high frequency surgical apparatus comprising a high frequency generator having at least one active electrode output and at least one neutral electrode output to which a part neutral electrode of a neutral electrode pair can be connected, with individual electrodes of the neutral electrode pair being connected to an auxiliary voltage with a significantly lower frequency than the high frequency, wherein a monitoring circuit produces from the auxiliary voltage and the auxiliary current flowing between the part neutral electrodes an impedance signal representative for the impedance between the two part neutral electrodes and transmits a high frequency generator blocking signal and/or an alarm signal on exceeding a first fixed upper alarm limit and/or a lower second upper alarm limit for the impedance signal, which can be matched to the actual value of the impedance signal. The invention also relates to a corresponding high frequency surgical apparatus.

DESCRIPTION OF PRIOR ART

When using high frequency surgical apparatus it is mainly the monopolar operating state which is selected, i.e. the high frequency current is supplied to the tissue via an active electrode and is led away via a large area neutral electrode, which is secured to a suitable position on the patient's body. In earlier times, this neutral electrode was generally executed as a unitary structure which lies at least substantially at the same potential in all areas. Since skin-burns can arise with incorrect application of the neutral electrode to the skin of the patient, and since bypass currents can flow away capacitively via the operator, it is particularly important to check the correct contact of the electrode.

Initial approaches to solve this problem with a single area electrode were not satisfactory. Accordingly, electrodes were provided which were equipped with two or more mutually insulated conductive surfaces by which measurement currents with a lower frequency than the high frequency (also including direct currents) could then be passed in addition to the high frequency current. These measurement currents were exploited in order to trigger an alarm when a predetermined threshold is exceeded, or to separate the high frequency generator from the electrode. Such circuits are, for example, described in EP 0 390 937 A1, in DE-OS 28 49 422 or in DE-OS 35 44 443. In these known solutions there is a fixedly adjusted limit which, if reached or exceeded, is regarded as meaning that the contact or transition resistance of the neutral electrode is no longer regarded as acceptable and an acoustic alarm is thereby triggered. The monitoring circuit is activated by plugging in the neutral electrode. A disadvantage of these known circuits lies in the fact that the alarm limit must lie relatively far from the actual operating values of the contact resistance. In addition, a large and entirely permissible variation of the normally prevailing contact resistances is also present with different constructional forms of the electrodes.

A circuit is also already known (U.S. Pat. No. 4,848,335) in which the momentarily present impedance between the neutral electrode and the tissue is determined by pressing a SET key and thereafter the alarm limit is set. In this manner differences in the nature of the skin of different patients and also differences in the type of construction of the neutral electrode can be taken into account on specifying the alarm limits. However, a disadvantage of the circuit lies in the fact that, when using split neutral electrodes with an adhesive layer, the resistance which is first determined on pressing the SET key directly after the application of the neutral electrode, and which is used to determine the alarm limit, is too high. This situation arises because the adhesive only gradually penetrates into the pores of the skin and the ideal operating transition resistance is only present at a later time, but can then no longer influence the position of the alarm limit.

A further prior known circuit (DE 32 39 640 C2) monitors the contact resistance between the two part electrodes fully automatically and changes the alarm limits automatically upwardly and downwardly with slow changes of the contact resistance. The disadvantage of this circuit is that with slow changes of the transition impedance, such as also arise with a slow, undesired release of the neutral electrode of the patient, the alarm limits can be set to more sensitive values unnoticed by the operator so that an alarm first takes place at a likewise provided fixed emergency alarm threshold which is just as far removed from the operating impedances as the initially mentioned previously known circuit with fixedly adjusted alarm limits.

OBJECT OF THE INVENTION

The object of the present invention is to provide a method of operating a radiofrequency surgical apparatus and a radiofrequency surgical apparatus of the initially named kind in which the variable alarm limit can be ideally adapted to the desired operating impedance by taking account of different electrode kinds and shapes and also different skin resistances of the patients, without a slow separation of the neutral electrode from the body of the patient first being noted at a fixed upper alarm limit, i.e. an emergency alarm threshold.

BRIEF DESCRIPTION OF THE INVENTION

In order to satisfy this object there is provided a method of the initially named kind which is characterized in that the adaptation of the second alarm limit is effected by pressing a SET key. The corresponding apparatus is characterized in that a SET key is provided for the adaptation of the second alarm limit and, on being pressed, triggers an automatic adaptation to the actual impedance signal.

Thus, in accordance with the invention, on pressing a SET key, no instantaneous value is recorded but rather an impedance monitoring circuit is activated which, on sinking of the impedance between the neutral electrode pair and the skin in the sense of an improved contact, makes the variable second alarm limit sharper, i.e. shifts it to lower impedances.

If, in contrast, the impedance between the part electrodes increases, for example as a result of a partial separation from the skin of the patient, then in accordance with the invention the variable second alarm limit does not follow this change but rather in this case an alarm situation arises, i.e. this leads to a blocking of the radiofrequency generator (switching off of the electrode outputs) and/or to the transmission of an optical or acoustic alarm signal. The user must then determine whether the increase in resistance has been produced by normal changes at the patient's skin or by an undesired partial separation of the neutral electrode from the patient If an adequately good contact of a neutral electrode is determined or if a partly separated neutral electrode has again been secured to the patient in problem-free manner, then the operator actuates the SET key anew, whereby the second variable alarm limit is now newly adapted to the impedance value regarded as trouble-free between the two part electrodes.

As a result of the arrangement of the invention, the operator is thus forced by blocking of the radiofrequency generator and/or by an alarm, on an increase of the actual impedance, to inspect the neutral electrode and to assess whether the increase in impedance is brought about by a change of the impedance of the skin lying in the normal range or by a fault. This is an important safety aspect in clinical use. If a problem-free contact of the neutral electrode is determined, so that an increase in the skin resistance in the normal range is present, then the operator can set the alarm limit correspondingly higher by actuation of the SET key. An important feature of the invention is thus that the variable second alarm limit cannot be made more sensitive without conscious action on the part of the operator. In contrast, the increase in sensitivity of the second alarm limit takes place in accordance with the invention fully automatically without action on behalf of the operator.

A short circuit recognition means is also provided in accordance with the invention, which, when using single area or single pole neutral electrodes, continuously transmits a corresponding signal but which also responds when, on using two part neutral electrodes, a short circuit arises between the latter. The short circuit recognition means can, for example, take place by observing the wave-shape of the auxiliary voltage that is used, which changes in characteristic manner in the case of a short circuit, which can be exploited for the formation of a short circuit signal.

BRIEF LISTING OF THE FIGURES

FIG. 1 is a schematic block circuit diagram of a high frequency surgical apparatus in accordance with the invention, and FIG. 2 is a diagram which reproduces the time dependence of the impedance signal dependent on the impedance between the two part electrodes and of the two alarm limits of the invention.

DESCRIPTION OF PREFERRED EMBODIMENTS

Figure 1:
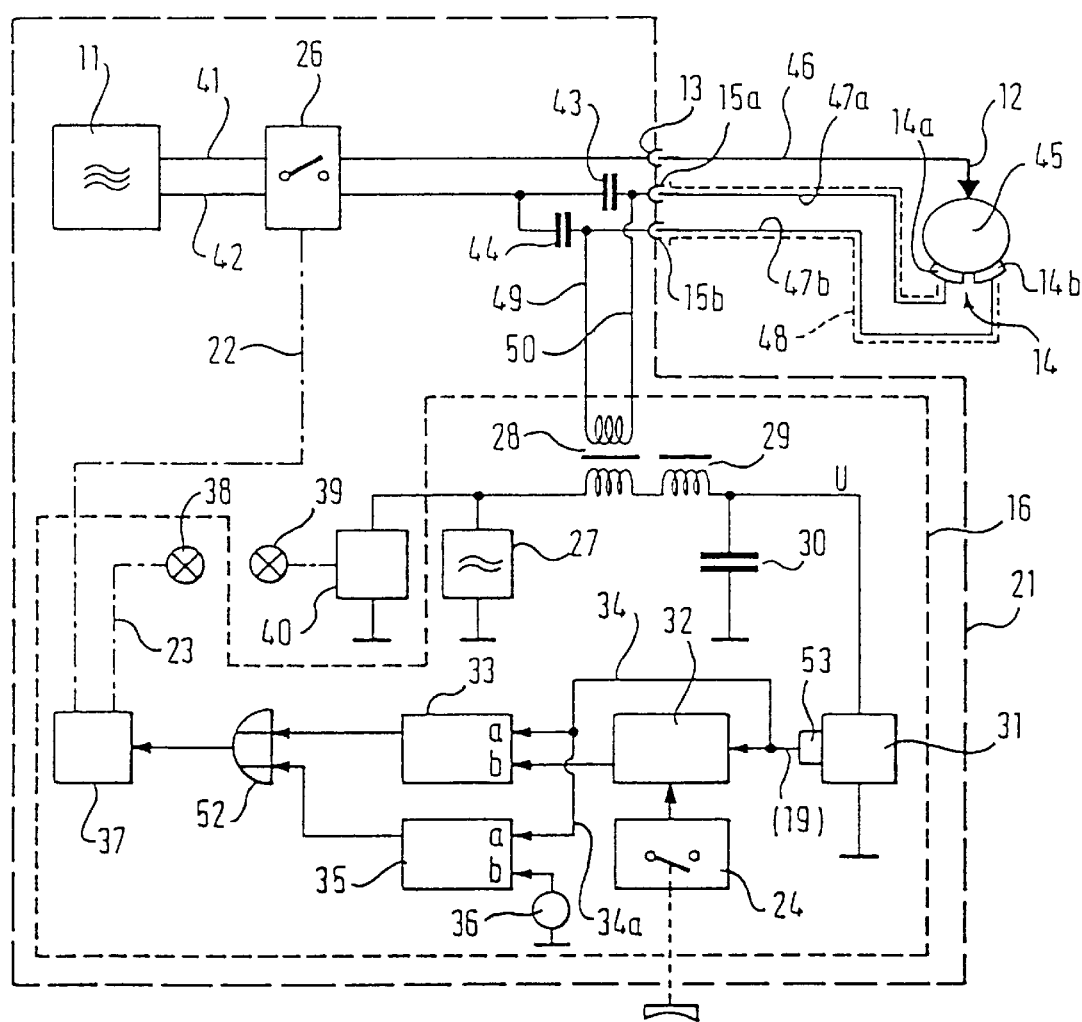

In accordance with FIG. 1 a high frequency surgical apparatus 21 in accordance with the invention contains a high frequency (radiofrequency) generator 11, the output lines 41, 42 of which are connected via a switching means 26 to an active electrode output 13 and via two separating capacitors 43 and 44 connected in parallel to an output 15a for a part neutral electrode and to an output 15b for a further part neutral electrode respectively. A separating capacitor or other galvanic separation can also be provided in the output line 41 between the high frequency generator 11 and the active electrode output 13.

A purely schematically indicated active electrode 12 is connected to the active electrode output 13 via a connection line 46 and can be brought by the surgeon into electrical contact with the body of a patient 45. To the part neutral electrode outputs 15a and 15b there are respectively connected connection lines 47a and 47b, which are combined into a cable 48 indicated in broken lines. The connection lines 47a and 47b respectively lead to part neutral electrodes 14a and 14b, which are electrically insulated from one another, and which together form a neutral electrode 14, which can be applied to a suitable position on the patient 45 and brought into electrical contact with his skin.

Whereas the neutral electrode 14 is fixedly but releasably attached to the patient 45 at a suitable position, the active electrode 12 is brought by the surgeon into connection with the tissue to be treated as required. In general, a switch actuatable by the surgeon is provided at the instrument containing the active electrode, via which the high frequency at the electrodes 12, 14 can be activated. This can also take place by means of a foot switch, which is not illustrated.

For the monitoring of a problem-free operation of the neutral electrode 14, a monitoring circuit 16 is provided in accordance with the invention as follows.

Lines 49 and 50 branch off between the two separating capacitors 43, 44 connected in parallel to the output line 42 and the part neutral electrode outputs 15a and 15b respectively, and lead to the output winding of a transformer 28, the primary winding of which is connected at one side to a low frequency auxiliary voltage source 27, which has for example an internal resistance of 1 kΩ and an auxiliary voltage of approximately 10 V, but a significantly lower frequency than that of the voltage transmitted by the high frequency generator 11. The frequency of the high frequency generator 11 can, for example, lie between 300 kH and 600 kH, while the frequency of the auxiliary voltage can, for example, amount to 15 kH.

An inductor 29 is connected to the terminal of the primary winding of the transformer 28 remote from the low frequency auxiliary voltage source 27 and is followed by a capacitor 30 which is connected to the preferably earthed other pole of the auxiliary voltage source 27. The inductor 29 and the capacitor 30 form a voltage divider.

In this manner a current circuit is formed, the current of which is coupled into the primary winding of the transformer 28 and flows to the part neutral electrodes 14a, 14b. The lower the impedance between the part neutral electrodes 14a, 14b, the more current flows and the higher is the voltage U at the connection point between the inductor 29 and the capacitor 30. The voltage U thus represents a measure of the impedance between the part neutral electrodes 14a, 14b, and indeed in the sense that the higher the impedance between the part neutral electrodes 14a, 14b, the lower is the voltage U.

The connection point between the inductor 29 and the capacitor 30 is connected to a voltage measurement apparatus 31, at the output of which a voltage signal U appears, the inversion of which represents an impedance signal representative for the impedance Z between the part neutral electrodes 14a, 14b. Although the voltage signal U can be, and preferably also is, directly evaluated, an inversion stage 53 which inverts the course of the voltage U is assumed to be applied to the voltage measurement apparatus 31 in FIG. 1 for a better understanding of the operation. Thus, an impedance signal 19 representative of the impedance between the part neutral electrodes 14a, 14b is present at the output of the inversion stage 53 and is applied both to the input of an adaptive memory 32 and also via lines 34, 34a to the inputs "a" of first and second comparators 33 and 35, the outputs of which are led to an OR-gate 52. The output of the adaptive memory 32 is applied to the second input "b" of the first comparator 33.

The adaptive memory 32 is so designed that after pressing the SET key 24 at a time $t_1$ in accordance with FIG. 2 it stores an alarm limit value 20 which lies by a predetermined amount 25 above the actual impedance signal 19. At the output of the memory 32 there thus appears a corresponding alarm limit signal. As soon as a predetermined increment 18 has been added to the amount 25, then an alarm limit reduced by this increment 18 is stored. This successive storage of step-like reducing alarm limits continues until a spacing or amount 25 is produced between the actual value of the impedance signal 19 and the previously stored alarm limit 20, which no longer becomes smaller and the alarm limits is thus maintained.

The output of the first comparator 33 delivers a zero signal to the one input of the OR-gate 52 when the signal at the input "a" is smaller than at the input "b". An L signal is delivered by the comparator 33 to the OR-gate 52 when the signal at the input "a" is greater than at the input "b".

The output of the second comparator 35 is applied to the second input of the OR-gate 52, which determines the fixed upper safety alarm limit 17 in that the impedance signal 19 is applied to its input "a" via the lines 34, 34a, and a fixed reference voltage source 36 is applied to the second input "b". The reference voltage of the reference voltage source 36 is so adjusted in the works that the two input signals at "a" and "b" are the same when an impedance signal corresponding to the upper alarm limit 17 is applied via the lines 34, 34a.

If the impedance signal at the input "a" of the second comparator 35 is smaller than the reference signal at the input "b", then a zero signal appears at the output of the comparator 35. If the signal of the input "a" is larger than the input signal at the input "b" determining the alarm limit 17, then an L signal appears at the output of the comparator 35.

The output of the OR-gate 52 is applied to an alarm circuit 37, which is connected via a high frequency blocking signal line 22 to the switching device 26 and via an alarm signal line 23 to an alarm signal generator 38 which is, for example, formed by an LED.

On the appearance of an L signal at one or both inputs of the OR-gate 52, a switching process is triggered by the alarm circuit 37 which separates the high frequency generator 11 from the electrode outputs 13, 15a, 15b by opening of the switch in the switching device 26 and/or causes the alarm signal generator 38 to respond.

As a result of the OR-linkage of the output signals of the comparators 33 and 35, it is ensured that an alarm is triggered when the fixed alarm limit 17 is exceeded and/or when the alarm limit 20 is exceeded.

By pressing the SET key 24, the adaptation procedure is started anew, whereupon the alarm limit is set to a new and in particular higher value, while the fixed upper alarm limit 17 represents a safety limit which can also not be exceeded by an influence exerted by the operator. It is only possible to achieve a situation in which, by suitable application of the neutral electrode 14, the actual impedance signal lies beneath the fixed alarm limit 17.

The circuit also has a short circuit recognition circuit 40, which is connected to the low frequency auxiliary voltage source 27 and which acts on a further alarm signal generator 39, which is likewise formed as an LED.

Further particulars of the described circuit can be seen from the functional description with reference to FIG. 2.

In FIG. 2 there is shown a typical course of an impedance signal 19 such as arises after the application of a neutral electrode 14 to a patient 45.

The relatively high actual impedance which lies above a first fixed alarm limit 17 when applying the neutral electrode 14 at the time point to sinks after a few seconds to values beneath the fixed alarm limit 17 determined by the comparator 35 and approximately reaches a minimum at a time $t_2$.

It should now be assumed that at a time $t_1$ after the application of the neutral electrode 14 the SET key 24 is pressed. In this way the adaptation process is started, commencing from a reset level 54 lying above the fixed alarm limit 17, and the second variable alarm limit 20 is fixed in such a way that it initially lies by a predetermined amount 25 above the actual impedance signal 19. This alarm limit 20 is initially retained in the active memory 32 until a predetermined hysteresis 18 has been added to the interval 25 between the alarm limit 20 and the actual impedance signal 19, whereupon a somewhat lower impedance value which again has the spacing 25 from the actual impedance signal 19 is now stored in the memory 32 and is again retained until the increment 18 has again been added to the interval 25.

This step-wise lowering of the alarm limit 20 in the adaptive memory 32 is continued until the actual impedance signal 19 reaches the minimum value or a constant value at the time $t_2$. From now on, the alarm limit 20 remains initially constant. If the actual impedance signal 19 exceeds the alarm limit 20 at the time $t_3$, then an alarm is initiated, i.e. the high frequency generator 11 is switched off from the output terminals 13, 15a, 15b by means of the switching device 26 and/or the alarm generator 38 responds. This alarm is maintained until the SET key is pressed anew.

When the operator has noted the switching off of the radiofrequency and/or perceived the alarm signal, then he can investigate the neutral electrode 14 and, in the event that he detects a problem-free seating on the body of the patient 45, can press the SET key 24 anew at the time $t_4$, whereupon, in the manner illustrated in FIG. 2, a new adaptation of the variable second alarm limit 20 to the actual value of the impedance signal 19 takes place, starting again from the reset level 54 and in analogous manner to that at the time $t_1$. The alarm limit 20 is thus first shifted to higher impedance values still beneath the upper limit 17 but then automatically adapts on renewed sinking of the impedance signal 19 to the actual impedance signal 19 so that the alarm limit 20 is again made sharper.

Should the actual impedance 19 exceed the first upper alarm limit 17, and the operator press the SET key, then the second comparator 35 prevents a renewed deblocking of the radiofrequency generator 11 or extinguishing of the alarm signal generator 38 as a result of the reference voltage of the reference voltage source 36, which is selected to correspond to the first alarm limit 17. Renewed operation is thus first possible when the actual impedance signal 19 has again fallen below the first alarm limit 17. This can, for example, be brought about by the operator by an improved attachment of the neutral electrode 14.

In FIG. 2 an arrow for the course of the voltage U at the output of the voltage measurement apparatus 31 is also applied to the ordinate. When the limits 17, 20 and the shape of the curve 19 are associated with the voltage U, the adaptive memory 32 and also the comparators 33 and 35 should be so modified that the size relationships of the individual values are selected to be directly the inverse of those described above, since the curves for the voltage U and the impedance R are directly opposite to those shown.

When a short circuit arises between the part neutral electrodes 14a, 14b or when a single area or single pole neutral electrode 14 is connected to the two electrode outputs 15a, 15b, the short circuit recognition circuit 40 recognizes a short circuit, which is indicated to the operator by response of the alarm signal generator 39.

REFERENCE NUMERAL LIST 11 high frequency generator
12 active electrode
13 active electrode output 14a neutral electrode
14b part neutral electrode
15a output for a part neutral electrode
15b output for a part neutral electrode
16 monitoring circuit
17 fixed upper alarm limit
18 increment
19 impedance signal
20 second variable alarm limit
21 high frequency surgical apparatus
22 high frequency blocking signal line
23 alarm signal line
24 SET key
25 predetermined interval
26 switching device
27 low frequency auxiliary voltage source
28 transformer
29 inductor
30 capacitor
31 voltage measurement apparatus
32 adaptive memory
33 first comparator
34 line
35 second comparator
36 reference voltage source
37 alarm circuit
38 alarm signal generator
39 alarm signal generator
40 short circuit recognition circuit
41 output line
42 output line
43 separating capacitor
44 separating capacitor
45 patient
46 connection line
47a connection line
47b connection line
48 cable
49 line
50 line
51 adjustable reference voltage source
52 OR-gate
53 inverting stage
54 reset level

We claim:

1. A method of operating a high frequency surgical apparatus comprising a high frequency generator having at least one active electrode output and at least one neutral electrode output to which one individual neutral electrode of a neutral electrode pair is connectable, with individual electrodes of the neutral electrode pair being connected to an auxiliary voltage with a significantly lower frequency than the high frequency produced by the high frequency generator, the method comprising the steps of:

producing from the auxiliary voltage and auxiliary current flowing between the two individual neutral electrodes an impedance signal representative of the impedance between the two individual neutral electrodes;

transmitting at least one of a high frequency generator blocking signal for blocking the high frequency generator and an alarm signal when the impedance signal exceeds at least one of a first fixed upper alarm limit and a lower second upper alarm limit for the impedance signal; and adapting the second upper alarm limit to the actual value of the impedance signal with actuation of a SET key by first resetting the second upper alarm limit to a value above the actual value of the impedance signal and up to or above the first upper alarm limit up to a maximum reset level, and subsequently adjusting the second upper alarm limit to a predetermined spacing from the actual value of the impedance signal.

2. A method in accordance with claim 1 wherein the second upper alarm limit is adjusted to the predetermined spacing from the actual value of the impedance signal in a step-wise manner.

3. A method in accordance with claim 1 wherein, after the second upper alarm limit is adjusted to the predetermined spacing from the actual value of the impedance signal, the second upper alarm limit is further adjusted to follow the impedance signal only when the impedance signal decreases.

4. A method in accordance with claim 3 wherein the second upper alarm limit is continuously adjusted to the predetermined spacing from the actual value of the impedance signal or; after the second upper alarm limit is adjusted to the predetermined spacing from the actual value of the impedance signal, the second upper alarm limit is held fixed until the actual value of the impedance signal has decreased by a specific increment from the fixed second upper alarm limit, whereupon the second upper alarm limit is further adjusted to the predetermined spacing from the actual value of the impedance signal.

5. A method in accordance with claim 1 wherein when the actual value of the impedance signal exceeds at least one of the first upper alarm limit and the second upper alarm limit during the adapting step, at least one of an alarm signal and a high frequency generator blocking signal for blocking the high frequency generator is triggered.

6. A method in accordance with claim 5 wherein the at least one of the alarm signal and the high frequency generator blocking signal is canceled only upon a renewed actuation of the SET key and subsequent adaptation of the second upper alarm limit to the actual value of the impedance signal, provided the actual value of the impedance signal is lower than the first upper alarm limit.

7. A method in accordance with claim 1 further comprising the step of providing a short circuit recognition to perform at least one of distinguishing and indicating the use of one individual neutral electrode instead of two individual neutral electrodes.

8. A high frequency surgical apparatus comprising:

two individual neutral electrodes;

a high frequency generator having at least one active electrode output and at least one neutral electrode output to which at least one individual neutral electrode of the two individual neutral electrodes is connectable, with the two individual neutral electrodes being connected to an auxiliary voltage having a significantly lower frequency than the high frequency generated by the high frequency generator; and a monitoring circuit which produces from the auxiliary voltage and auxiliary current flowing between the two individual neutral electrodes an impedance signal representative of the impedance between the two individual neutral electrodes, and transmits at least one of a high frequency generator blocking signal and an alarm signal when the impedance signal exceeds at least one of a first fixed upper alarm limit and a lower second upper alarm limit for the impedance signal, the monitoring circuit including a SET key which is actuatable to trigger an automatic adaptation of the second upper alarm limit to the actual value of the impedance signal by resetting the second upper alarm limit to a value above the impedance signal and up to or above the first upper alarm limit up to a reset level, and subsequently automatically adjusting the second upper alarm limit to a predetermined spacing from the actual value of the impedance signal.

9. An apparatus in accordance with claim 8 wherein the second upper alarm limit is adjusted to the predetermined spacing from the actual value of the impedance signal in a step-wise manner.

10. An apparatus in accordance with claim 8 wherein the second upper alarm limit is subsequently automatically adjusted to follow the actual value of the impedance signal only when the impedance signal decreases.

11. An apparatus in accordance with claim 10 wherein the second upper alarm limit is continuously adjusted to the predetermined spacing from the actual value of he impedance signal or; after the second upper alarm limit is adjusted to the predetermined spacing from the actual value of the impedance signal, the second upper alarm limit is held fixed until the actual value of the impedance signal has decreased by a specific increment from the fixed second upper alarm limit, whereupon the second upper alarm limit is further adjusted to the predetermined spacing from the actual value of the impedance signal.

12. An apparatus in accordance with claim 11 further comprising a switching apparatus and an alarm signal generator, and wherein when the actual value of the impedance signal exceeds at least one of the first upper alarm limit and the second upper alarm limit during the automatic adaptation, the monitoring circuit transmits at least one of an alarm signal to the alarm signal generator and a high frequency generator blocking signal to the switch apparatus for blocking the high frequency generator.

13. An apparatus in accordance with claim 12 wherein the at least one of the alarm signal and the high frequency generator blocking signal is canceled only upon a renewed actuation of the SET key and subsequent adaptation of the second upper alarm limit to the actual value of the impedance signal, provided the actual value of the impedance signal has decreased below the first upper alarm limit.

14. An apparatus in accordance with claim 8 wherein the monitoring circuit further comprises short circuit recognition means for performing at least one of distinguishing and indicating the use of a one-piece neutral electrode instead of a multi-piece neutral electrode.

15. An apparatus in accordance with claim 8 wherein the monitoring circuit has a transformer and a low frequency auxiliary voltage source for applying the auxiliary voltage to the two individual neutral electrodes via the transformer.

16. An apparatus in accordance with claim 15 wherein the monitoring circuit includes an inductor, a capacitor, and a voltage measurement apparatus, wherein the transformer is connected in series with the inductor and the capacitor, and wherein the voltage measurement apparatus is configured for measuring the voltage at the connection point between the inductor and the capacitor representing an inverse pulse or impedance signal.

17. An apparatus in accordance with claim 16 wherein the monitoring circuit includes a first comparator and an adaptive memory for receiving the voltage signal or the impedance signal to produce an output signal which is applied to a first input of the first comparator, and wherein the voltage signal or the impedance signal is applied to the second input of the first comparator.

18. An apparatus in accordance with claim 17 wherein the monitoring circuit includes a second comparator for defining the first upper alarm limit, the second comparator receiving at a first input the voltage signal or the impedance signal and at a second input a fixed reference voltage.

19. An apparatus in accordance with claim 18 further comprising a switching device and an alarm signal generator, wherein the monitoring circuit includes an OR-gate and an alarm circuit, wherein outputs of the first and second comparators are connected to the OR-gate followed by at least one of the alarm circuit and the alarm signal generator, the switching device being connected to the alarm circuit and being disposed between the high frequency generator and electrode outputs for the active and neutral electrodes.

20. An apparatus in accordance with claim 8 further comprising a short circuit recognition circuit and an alarm signal generator, wherein the monitoring circuit has an auxiliary voltage source, the short circuit recognition circuit being connected with the auxiliary voltage source and energizing the alarm signal generator.

21. An apparatus in accordance with claim 8 wherein the two individual neutral electrodes are provided in a common insulated carrier having two mutually insulated conductive surfaces.

22. An apparatus in accordance with claim 8 wherein the two individual neutral electrodes are separate.

\* \* \* \* \*

UNITED STATES PATENT AND TRADEMARK OFFICE
CERTIFICATE OF CORRECTION

PATENT NO. : 5,971,981
DATED : October 26, 1999
INVENTOR(S) : Wolfram Hill, et. al.

It is certified that error appears in the above-identified patent and that said Letters Patent is hereby corrected as shown below:

Title page, item [73], Assignee: should read --Gebrüder Berchtold GmbH & Co.--

After "[22] Filed ...", insert -- [30] Foreign Application Priority Data
        Oct. 18, 1996 [DE] German Pat. Off. ......... 19643127.1 --

Signed and Sealed this

Fifth Day of December, 2000

Attest:

Q. TODD DICKINSON

*Attesting Officer*      *Director of Patents and Trademarks*